United States Patent [19]

Bohn et al.

[11] Patent Number: 4,594,328
[45] Date of Patent: Jun. 10, 1986

[54] TISSUE PROTEIN PP$_{21}$, A PROCESS FOR OBTAINING IT AND ITS USE

[75] Inventors: Hans Bohn, Marburg; Wilhelm Winckler, Wenkbach, both of Fed. Rep. of Germany

[73] Assignee: Hoechst Aktiengesellschaft, Fed. Rep. of Germany

[21] Appl. No.: 714,495

[22] Filed: Mar. 21, 1985

[30] Foreign Application Priority Data

Mar. 23, 1984 [DE] Fed. Rep. of Germany ....... 3410694

[51] Int. Cl.$^4$ ..................... C07K 15/14; A61K 35/42; A61K 35/50; A61K 39/395
[52] U.S. Cl. .................................... 436/543; 530/394; 530/395; 424/85; 424/95; 424/105; 436/536; 436/547; 435/7
[58] Field of Search ....................... 260/112 B, 112 R; 424/85, 95, 105; 436/536, 543, 547; 435/7

[56] References Cited

U.S. PATENT DOCUMENTS

| | | | |
|---|---|---|---|
| 4,041,021 | 8/1977 | Bohn | 260/112 B |
| 4,217,339 | 8/1980 | Bohn et al. | 260/112 B X |
| 4,309,339 | 1/1982 | Haupt et al. | 260/112 B |
| 4,524,027 | 6/1985 | Bohn | 260/112 R |

*Primary Examiner*—Howard E. Schain
*Attorney, Agent, or Firm*—Finnegan, Henderson, Farabow, Garrett & Dunner

[57] ABSTRACT

The protein PP$_{21}$ which has the following characteristics:

(a) an electrophoretic mobility in the region of that of $\beta_1$-globulins,
(b) an isoelectric point of 4.6±0.3;
(c) a sedimentation coefficient s$_{20,w}$ of 3.2±0.2 S;
(d) a molecular weight determined in an ultracentrifuge of 52,900±6,200;
(e) an extinction coefficient $E_1$ $_{cm}^{1\%}$(280 nm) of 10.5±1.0; and
(f) a carbohydrate fraction of 19.2±5.2 g/100 g (mannose 1.8±0.4, galactose 4.3±1.0, fucose 1.3+0.3, N-acetylglucosamine 6.5±2.0 and N-acetylneuraminic acid 5.3±1.5, each g/100 g), and a specified amino acid composition, a process for obtaining it and its use are described.

12 Claims, 2 Drawing Figures

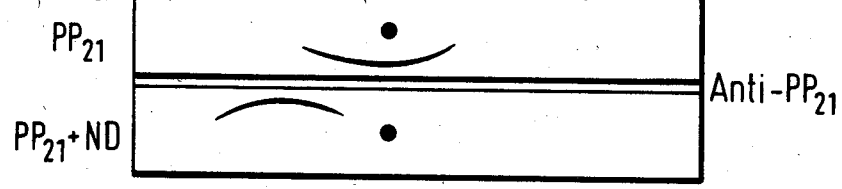

TISSUE PROTEIN PP21, A PROCESS FOR OBTAINING IT AND ITS USE

The invention relates to a tissue protein, which is called PP21, and to a process for obtaining it. PP21 can be used to prepare antisera which can be employed to detect and determine PP21 in tissue and in body fluids. The detection and determination of PP21 have diagnostic significance. They can be employed to diagnose diseases in particular organs, to monitor the course of an illness or to check a therapy.

Although proteins are known to the state of the art, including tissue proteins, none of them have the properties indicated below for PP21.

The invention relates to the protein PP21 which has the following characteristics
(a) an electrophoretic mobility in the region of that of $\beta_1$-globulins;
(b) an isoelectric point of 4.6±0.3;
(c) a sedimentation coefficient $s_{20,w}$ of 3.2±0.2 S;
(d) a molecular weight determined in an ultracentrifuge of 52,900±6,200;
(e) an extinction coefficient $E_{1cm}^{1\%}(280\ nm)$ of 10.5±1.0; and
(f) a carbohydrate fraction of 19.2±5.2 g/100 g (mannose 1.8±0.4, galactose 4.3±1.0, fucose 1.3±0.3, N-acetylglucosamine 6.5±2.0 and N-acetylneuraminic acid 5.3±1.5, each g/100 g).

The amino acid composition of PP21 is indicated in the table below:

| Amino acid | Residues per 100 residues | Coefficient of variation |
|---|---|---|
| lysine | 8.75 | 3.91 |
| histidine | 1.58 | 6.81 |
| arginine | 2.75 | 6.07 |
| aspartic acid | 9.59 | 1.97 |
| threonine | 3.73 | 7.22 |
| serine | 7.43 | 5.95 |
| glutamic acid | 8.16 | 5.15 |
| proline | 11.34 | 9.36 |
| glycine | 7.01 | 1.25 |
| alanine | 4.98 | 3.62 |
| cystine ½ | 5.50 | 0.84 |
| valine | 8.14 | 1.42 |
| methionine | 0.00 | 0.00 |
| isoleucine | 4.86 | 2.78 |
| leucine | 5.42 | 10.34 |
| tyrosine | 5.01 | 5.01 |
| phenylalanine | 3.56 | 1.00 |
| tryptophan | 2.12 | 17.65 |

The following may be stated to explain the characterizing features of the tissue protein:

The electrophoretic mobility was determined in the micro modification on cellulose acetate films (supplied by Sartorius) using sodium diethylbarbiturate buffer, pH 8.6, and a Microzone R 200 apparatus from Beckman Instruments.

The isoelectric point was determined using a column (440 ml) supplied by LKB, Stockholm. The Ampholin ® mixture had a pH range of 4.0 to 6.0.

The sedimentation coefficient was determined in an analytical ultracentrifuge supplied by Beckman (Spinco Apparatus, Model E) at 60,000 rpm, in double-sector cells using the UV scanner technique at 280 nm. The solvent used was water. The protein concentration was 0.2 g/100 ml.

The sedimentation equilibrium method was used to determine the molecular weight in an ultracentrifuge. The concentration of the protein was set at about 1.0 0.D. (optical density) for this purpose. The solvent used was a 0.05 mol/l phosphate buffer (pH 6.8) which contained 0.2 mol/l NaCl. The determination was carried out at 9,000 rpm. Recording was carried out with UV optics at 280 nm, using a photoelectric scanner.

For the determination of the extinction coefficient, the substance was dissolved in distilled water to a concentration of 1 g/l.

The analysis of the carbohydrates was carried out as follows: after hydrolysis of the glycosidic bonds, the liberated neutral sugars were separated as the borate complexes on an anion exchanger column (Y. C. Lee et al., Anal.Biochem. (1969), 27, 567), stained in the eluate by admixture of Cu(I) bicinchoninate reagent (K. Mopper and M. Gindler, Anal.Biochem. (1973), 56, 440), and determinated quantitatively using rhamnose as the internal standard. The amino sugars were detected and determined by their reaction with ninhydrine. The content of neuraminic acid was determined by the method of Warren (Methods in Enzymology, (1963), Vol.VI, 463–465).

The amino acid analysis was carried out by the method of S. Moore et al., Anal.Chem. (1958), 30, 1185, using a Multichrom B liquid chromatograph supplied by Beckman. ½ cystine was determined as cysteic acid following oxidation of the proteins with performic acid (S. Moore et al., Anal.Chem. (1958), 30, 1185) and subsequent chromatography (S. Moore, J.Biol.Chem. (1963), 238, 235). The tryptophan content was found by direct photometric determination by the method of H. Edelhoch, Biochemistry (1967), 6, 1948.

On investigation of extracts from various human organs, PP21 was detected in the placenta, in the stomach, in the intestinal tract (colon, jejunum), in the bladder and in the spleen. Extracts of other human organs, such as heart, lung, liver, skin, kidney, adrenal and uterus, either did not contain this protein or contained only traces of it.

Human organs in which PP21 is found can be used for the isolation of this protein. Particularly suitable for this are fully developed human placentae, which are produced in ample amounts and which contain the protein in sufficiently high concentrations. It is possible to extract with physiological salt solution an average of 7 mg of PP21 from a fully developed human placenta (600 g).

An antigen which has an immunochemical behavior like that of PP21 is, moreover, a constituent of the so-called MP2 proteins of the human placenta. The MP2 proteins are a group of tissue proteins of complex composition, which are apparently membrane-associated in the placenta. They are obtained from the residue of placental tissue, which is insoluble after washing with physiological salt solution, by treatment with solubilizing agents, for example with the non-ionic detergent Triton ® X-100.

Their isolation and characterization have been described in German patent application No. 3,334,405, filed on Sept. 23, 1983. The MP2 have molecular weights between 200,000 and more than 1 million. Their structure involves a total of at least four different components which differ in their antigenic determinants. Once of these components, called C, is immunochemically indistinguishable from the soluble tissue protein PP21 described in the present application.

PP$_{21}$ has the following properties which can be utilized in a process for isolating it, by employing measures appropriate for these properties:

(1) it is precipitated from aqueous solutions with ammonium sulfate at a pH of 6–8 and 30–60% saturation;

(2) it is precipitated with acridine bases which are soluble in water, for example 2-ethoxy-6,9-diaminoacridine lactate, at pH values between 7 and 9 and a concentration of the base of 4 to 8 g/l, but is not or is hardly precipitated at pH 6.0 when the concentration of the base is 4 g/l or less;

(3) on addition of ethanol to dilute salt solutions, for example 10–20 g/l NaCl solution, in which it is dissolved, at pH 7 the major part of it remains in the supernatant up to a concentration of 200 ml of alcohol per liter;

(4) on electrophoretic fractionation at pH 7–9, it is found in the region of the $\beta_1$-globulins;

(5) on isoelectric focusing in the pH range 4.3 to 4.9, most of it appears between 4.4 and 4.8;

(6) on gel filtration with Sephade it behaves like proteins having molecular weights from 40,000 to 100,000;

(7) it can be bound to weakly basic ion exchangers, for example DEAE-cellulose of DEAE-SephadexR, at a conductivity of about 0–2 mS and a pH of about 7 to 9, and can be eluted with more concentrated salt solutions, for example 10–50 g/l NaCl solutions;

(8) it can be concentrated and isolated from an aqueous solution by immunoadsorption.

Accordingly, the invention also relates to a process for obtaining or concentrating PP$_{21}$, which comprises subjecting an extract which has been obtained, using a dilute salt or buffer solution, from organs which contain this protein to one or more of the following measures:

(a) precipitation of the protein PP$_{21}$ using ammonium sulfate in the pH range 6 to 8 and at 30–60% saturation;

(b) precipitation of accompanying proteins using an acridine base which is soluble in water, at a pH of 6 and a concentration of the base of 4 g/l or less, or precipitation of the protein PP$_{21}$ using an acridine base which is soluble in water, at a pH between 7 and 9 and a concentration of the base of 4 to 8 g/l;

(c) precipitation of accompanying proteins by addition of up to 200 ml of ethanol per liter at pH 7;

(d) preparative zone electrophoresis, the protein fraction having a mobility in the region of that of $\beta_1$-globulins being obtained;

(e) isoelectric focusing, the proteins in the pH range 4.4–4.8 being obtained;

(f) gel filtration or ultrafiltration, the proteins in the molecular range 40,000 to 100,000 being obtained;

(g) adsorption onto a weakly basic ion exchanger, and elution of the protein PP$_{21}$;

(h) concentration by immunoadsorption.

Apart from ammonium sulfate, it is of course also possible to use for the precipitation of PP$_{21}$ other neutral salts which are customarily used in preparative biochemistry. Apart from an acridine base, it is also possible to use a water-soluble derivative of a quinoline base, as are known for protein fractionations, within the scope of the process according to the invention. For the isolation of the protein, as appropriate for its electrophoretic behavior, its isoelectric point or its molecular weight, it is also possible to use other measures which are suitable to separate a protein having the indicated properties from other proteins. The various methods of preparative electrophoresis, isoelectric focusing, gel filtration, gel chromatography or ultrafiltration, or the property of PP$_{21}$ of being capable of binding to weakly basic ion exchangers and being eluted again from them, can be used for this purpose.

PP$_{21}$ can be isolated by appropriate combination of the abovementioned measures which concentrate PP$_{21}$ or separate this protein from other proteins.

Accordingly, the present invention is regarded as relating to the individual steps for the concentration of PP$_{21}$ and to the process for the purification of PP$_{21}$ resulting from combination of the measures for concentration.

The steps for the concentration and isolation of PP$_{21}$ which are indicated in the Example are by no means all obligatory, nor need they be carried out in the sequence described in this Example.

It might be possible to use the extract from human placentae directly for immunoadsorption. However, since the concentration of PP$_{21}$ in the placental extract is relatively low, it is advantageous, by a preliminary fractionation of the extract, first specifically to concentrate the protein PP$_{21}$ using methods which are suitable for the fractionation of proteins on a relatively large scale; for example by fractional precipitation using natural salts or organic cations, by gel filtration or by ion exchange chromatography. In addition, the immunoadsorption step might be replaced by use of other methods of separation, for example by preparative electrophoresis or isoelectric focusing.

Gel filtration on Ultragel ® AcA 34 and inverse immunoadsorption have proved useful for the final purification of PP$_{21}$ in the last stage of isolation.

Apart from the parameters indicated, it is also possible to use immunochemical methods for the detection and determination of PP$_{21}$, for example in a fraction from a separation operation, since PP$_{21}$ has antigenic properties.

An antiserum suitable for the immunochemical detection of PP$_{21}$ was first obtained by immunization of rabbits with the membrane-associated proteins MP$_2$ of the placenta. The antisera which were thus obtained contained antibodies against at least four different antigenic components (A, B, C and D) in the MP$_2$ proteins. It was found that the antibodies against component C also precipitate with a soluble protein from the placenta, namely with the tissue protein PP$_{21}$ which is described in the present application.

The anti-MP$_2$ rabbit sera could be used, on the one hand, for the immunological detection of PP$_{21}$ in soluble protein fractions of the placenta and, on the other hand, for the preparation of an immunoadsorbent for the concentration and isolation of PP$_{21}$ from soluble placental protein fractions. This was possible because the other antigenic components involved in the structure of the MP$_2$ proteins are not found, or are found in not more than traces, in the soluble placental protein fractions.

Monospecific antisera can be prepared using the purified PP$_{21}$, which has been obtained in accordance with the present application, by immunization of animals by known methods.

FIG. 1a shows the immunological reaction of PP$_{21}$ (treated or untreated with the enzyme neuraminidase (ND) from Vibrio,), with a specific antiserum from rabbits, after fractionation in a agar-containing gel in an electric field. The untreated native protein is found in the region of the $\beta_1$-globulins; the protein becomes more basic on elimination of the neuraminic acid and then appears in the region of the $\gamma$-globulins.

FIG. 1b shows, for the purpose of comparison, fractionation of the proteins in the serum, visualized by their immune reaction with an antiserum from rabbits against human serum (HS).

It is also possible to use the Ouchterlony gel diffusion technique (see Schultze and Heremans, Molecular Biology of Human Proteins, Vol. 1, p. 134) or, if necessary, more sensitive methods, such as radioimmunoassays or enzyme immunoassays, for the immunological detection of $PP_{21}$.

The detection and determination of $PP_{21}$ have diagnostic importance. $PP_{21}$ is a tissue protein which is found in relatively large concentrations only in certain organs. Where these organs are diseased, the concentration of the tissue protein $PP_{21}$ in the serum or in other body fluids of the patients can increase above normal as a result of increased cell destruction. Thus, the detection and determination of $PP_{21}$ in body fluids can be used for the diagnosis of diseases of these organs or as markers for monitoring the course of the illness and for checking the therapy.

Hence $PP_{21}$ can be used to prepare antisera which can be employed for the detection and determination of $PP_{21}$.

The invention is illustrated by the examples which follow:

EXAMPLE 1

(A) Extraction of the placentae and fractionation of the extract using an acridine derivative and ammonium sulfate 1,000 kg of deep-frozen, mature human placentae were comminuted in a cutter-mixer and extracted with 1,000 liters of a 4 g/l saline solution. After removal of the tissue residue by centrifugation, the pH of the extract was adjusted to 6.0 with a 200 ml/l acetic acid solution, and, with stirring, 200 liters of a 30 g/l solution of 2-ethoxy-6,9-diaminoacridine lactate (Hoechst AG) were added. The precipitate was removed by centrifugation and discarded. 10 g/l Betonit A (supplied by Erbslöh and Co., Geisenheim/Rhine) were added to the supernatant, and the pH was adjusted to 7.0 by addition of 2N NaOH, and the mixture was filtered. 300 g/l ammonium sulfate were added slowly to the filtrate, with stirring; this resulted in the placental protein $PP_{21}$ precipitating out together with other proteins. The precipitate was filtered off; about 12 kg of a moist paste were obtained, and this is called fraction A below.

(B) Gel filtration on Sephadex G-150

500 g of fraction A were dissolved in about 400 ml of water and dialysed against a 0.1 mol/l tris HCl buffer (pH 8.0) which contained 1 mol/l NaCl and 1 g/l $NaN_3$ (buffer solution II). The protein-containing solution was applied to a column (20×100 cm) packed with Sephadex G-150, and underwent gel filtration. A 0.1 mol/l tris HCl buffer, pH 8, containing 1 mol/l NaCl and 1 g/l $NaN_3$ (buffer solution II) was used to elute. The eluates were tested in the Ouchterlony gel diffusion test using an anti-$MP_2$ rabbit serum to $PP_{21}$. The fractions which contained relatively large amounts of $PP_{21}$ were collected (molecular weight range between 40,000 and 100,000). The proteins were then precipitated by addition of 300 g/l solid ammonium sulfate. The precipitate was dissolved in water and dialysed against buffer solution II (fraction B).

(C) Concentration of $PP_{21}$ by immunoadsorption

1. Preparation of an anti-$MP_2$ rabbit serum Obtaining antibodies against $PP_{21}$ Antisera which contain antibodies against $PP_{21}$ were obtained by immunization of rabbits using the high molecular weight fraction (sedimentation coefficient approximately equal to or larger than 20 S) of the $MP_2$ proteins (German patent application No. 3,334,405). The immunization was carried out for a period of six weeks, using aluminum hydroxide as adjuvant, and was carried out as follows. The high molecular weight $MP_2$ fraction was dissolved in physiological saline solution (concentration 0.06 mg/3 ml) and the suspension was formed by stirring with the addition of aluminum hydroxide. The rabbits received 0.06 mg of protein in 3 ml of suspension/animal injected i.v. on each of the five consecutive days. This was followed by an interval of nine days. Then immunization was again carried out on five consecutive days with the abovementioned amount of antigen, again followed by an interval of nine days, and finally 0.06 mg of the antigen was once more injected on each of five consecutive days. The animals were exsanguinated after another period of seven to nine days had elapsed. After the blood had coagulated, the serum was obtained from the blood clot by centrifugation.

2. Preparation of the immunoadsorbent 300 ml of an anti-$MP_2$ serum from rabbits was dialyzed against a 0.02 mol/l phosphate buffer (pH 7.0) and chromatographed on DEAE-cellulose to remove the immunoglobulins. In this chromatography, the immunoglobulins migrate unhindered through the DEAE-cellulose, while the major part of the remaining serum proteins are absorbed onto the DEAE-cellulose. The immunoglobulin fraction in the eluate (4.78 g of protein) was then reacted with 478 g of specially purified agarose in the form of beads (Sepharose 4 B supplied by Pharmacia, Uppsala, Sweden), which had been activated with 59.9 g of cyanogen bromide, and it was thus covalently bonded to a support. The process is described by, for example, Axen et al., Nature 214, 1302 (1967). It was possible to isolate the protein $PP_{21}$ from a solution containing it, in particular from placental fractions concentrated in $PP_{21}$, using an immunoadsorbent prepared in this manner.

3. Procedure for the immunoadsorption

The immunoadsorbent was suspended in buffer solution II, packed into a chromatography column (5.5×20 cm) and washed with buffer solution II. Then half the amount of fraction B was applied to the column, whereupon $PP_{21}$ was bound by immunoadsorption. The column was thoroughly washed with buffer II. The adsorbed protein was then eluted from the column using about 600 ml of 6 mol/l urea solution. The eluates containing $PP_{21}$ were dialyzed against buffer solution II, and concentrated to about 10 ml in an ultrafilter. Yield per adsorption about 10 mg of $PP_{21}$.

Immediately after the elution of $PP_{21}$, the adsorbent in the column was again thoroughly washed with buffer solution II; it was then again used for the binding of $PP_{21}$ by immunoadsorption.

(D) Final purification of $PP_{21}$

The protein obtained by immunoadsorption was frequently contaminated by non-specifically bound serum proteins and other placental proteins. The major part of the accompanying serum proteins was removed by gel filtration on Ultrogel ® AcA 34. The remaining accompanying proteins were then removed by inverse or negative immunoadsorption, that is to say using carrier-bound antibodies against the proteins which were still present as contaminants. These were essentially serum immunoglobulins and traces of placental tissue protein $MP_1$.

We claim:

1. A protein $PP_{21}$, extracted from a source of said protein and having the following characteristics:
   (a) an electrophoretic mobility in the region of that of $\beta_1$-globulins;
   (b) an isoelectric point of $4.6\pm0.3$;
   (c) a sedimentation coefficient $s_{20,w}$ of $3.2\pm0.2$ S;
   (d) a molecular weight determined in an ultracentrifuge of $52,900\pm6,200$;
   (e) an extinction coefficient $E_{1cm}^{1\%}(280\ nm)$ of $10.5\pm1.0$;
   (f) a carbohydrate fraction of $19.2\pm5.2$ g/100 g (mannose $1.8\pm0.4$, galactose $4.3\pm1.0$, fucose $1.3\pm0.3$, N-acetylglucosamine $6.5\pm2.0$ and N-acetylneuraminic acid $5.3\pm1.5$, each g/100 g); and
   (g) an amino acid composition as in the following table:

| Amino acid | Residues per 100 residues | Coefficient of variation |
| --- | --- | --- |
| lysine | 8.75 | 3.91 |
| histidine | 1.58 | 6.81 |
| arginine | 2.75 | 6.07 |
| aspartic acid | 9.59 | 1.97 |
| threonine | 3.73 | 7.22 |
| serine | 7.43 | 5.95 |
| glutamic acid | 8.16 | 5.15 |
| proline | 11.34 | 9.36 |
| glycine | 7.01 | 1.25 |
| alanine | 4.98 | 3.62 |
| cystine ½ | 5.50 | 0.84 |
| valine | 8.14 | 1.42 |
| methionine | 0.00 | 0.00 |
| isoleucine | 4.86 | 2.78 |
| leucine | 5.42 | 10.34 |
| tyrosine | 5.01 | 5.01 |
| phenylalanine | 3.56 | 1.00 |
| tryptophan | 2.12 | 17.65 |

2. A process for obtaining or concentrating $PP_{21}$ as claimed in claim 1, which comprises subjecting an extract which has been obtained, using a dilute salt or buffer solution, from at least one organ which contains this protein to one or more of the following measures:
   (a) precipitation of the protein $PP_{21}$ using ammonium sulfate in the pH range 6 to 8 and at 30–60% saturation;
   (b) precipitation of accompanying proteins using an acridine base which is soluble in water, at a pH of 6 and a concentration of the base of 4 g/l or less, or precipitation of the protein $PP_{21}$ using an acridine base which is soluble in water, at a pH between 7 and 9 and a concentration of the base of 4 to 8 g/l;
   (c) precipitation of accompanying proteins by addition of up to 200 ml of ethanol per liter at pH 7;
   (d) preparative zone electrophoresis, the protein fraction having a mobility in the region of that of $\beta_1$-globulins being obtained;
   (e) isoelectric focusing, the proteins in the pH range 4.4–4.8 being obtained;
   (f) gel filtration or ultrafiltration, the proteins in the molecular range of 40,000 to 100,000 being obtained;
   (g) adsorption onto a weakly basic ion exchanger, and elution of the protein $PP_{21}$; and
   (h) concentration by immunoadsorption, to obtain or concentrate said $PP_{21}$ protein.

3. The process of claim 2, wherein said organ is selected from the group consisting of placenta, stomach, intestines, bladder and spleen.

4. A process for isolating the protein $PP_{21}$ of claim 1 comprising the steps of subjecting a liquid containing said protein $PP_{21}$ to at least one known procedure for isolating proteins, and, in each instance, recovering that material containing said protein $PP_{21}$.

5. The protein of claim 1, said protein being extracted from an organ or an extract of an organ.

6. The protein $PP_{21}$ of claim 5, said protein being extracted from a placenta or an extract of a placenta.

7. The protein $PP_{21}$ of claim 6, said protein being substantially pure.

8. The protein $PP_{21}$ of claim 1, wherein said protein is isolated and concentrated.

9. An antiserum to the protein of claim 1 obtained by immunizing an animal with the protein $PP_{21}$ and recovering said antiserum.

10. A method for detecting and determining protein $PP_{21}$ comprising the step of utilizing an effective amount of the antiserum of claim 9.

11. A substantially pure protein $PP_{21}$, with the following characteristics:
    (a) an electrophoretic mobility in the region of that of $\beta_1$-globulins;
    (b) an isoelectric point of $4.6\pm0.3$;
    (c) a sedimentation coefficient $s_{20,w}$ of $3.2\pm0.2$ S;
    (d) a molecular weight determined in an ultracentrifuge of $52,900\pm6,200$;
    (e) an extinction coefficient $E_{1cm}^{1\%}(280\ nm)$ of $10.5\pm1.0$;
    (f) a carbohydrate fraction of $19.2\pm5.2$ g/100 g (mannose $1.8\pm0.4$, galactose $4.3\pm1.0$, fucose $1.3\pm0.3$, N-acetylglucosamine $6.5\pm2.0$ and N-acetylneuraminic acid $5.3\pm1.5$, each g/100 g); and
    (g) an amino acid composition as in the following table:

| Amino acid | Residues per 100 residues | Coefficient of variation |
| --- | --- | --- |
| lysine | 8.75 | 3.91 |
| histidine | 1.58 | 6.81 |
| arginine | 2.75 | 6.07 |
| aspartic acid | 9.59 | 1.97 |
| threonine | 3.73 | 7.22 |
| serine | 7.43 | 5.95 |
| glutamic acid | 8.16 | 5.15 |
| proline | 11.34 | 9.36 |
| glycine | 7.01 | 1.25 |
| alanine | 4.98 | 3.62 |
| cystine ½ | 5.50 | 0.84 |
| valine | 8.14 | 1.42 |
| methionine | 0.00 | 0.00 |
| isoleucine | 4.86 | 2.78 |
| leucine | 5.42 | 10.34 |
| tyrosine | 5.01 | 5.01 |
| phenylalanine | 3.56 | 1.00 |
| tryptophan | 2.12 | 17.65 |

12. A method for diagnosing and monitoring a disease or monitoring the treatment of said disease, said disease being accompanied by an increase in the concentration of protein $PP_{21}$ comprising the step of utilizing in an immunochemical method the protein $PP_{21}$ of claim 1 to achieve said intended purpose with respect to said disease.

* * * * *

UNITED STATES PATENT AND TRADEMARK OFFICE
CERTIFICATE OF CORRECTION

PATENT NO. : 4,594,328
DATED : June 10, 1986
INVENTOR(S) : Hans Bohn and Wilhelm Winckler It is certified that error appears in the above-identified patent and that said Letters Patent is hereby corrected as shown below:

On the first page of the patent, change the designation of assignee from "HOECHST AKTIENGESELLSCHAFT" to --BEHRINGWERKE AKTIENGESELLSCHAFT--.

Signed and Sealed this

Eighteenth Day of November, 1986

Attest:

DONALD J. QUIGG

Attesting Officer     Commissioner of Patents and Trademarks